United States Patent
Zhang et al.

(10) Patent No.: US 9,250,257 B2
(45) Date of Patent: Feb. 2, 2016

(54) SAMPLE PROCESSING METHOD, DEVICE AND SYSTEM FOR AN ASSEMBLY LINE WORKSTATION

(71) Applicant: SHENZHEN MINDRAY BIO-MEDICAL ELECTRONICS CO., LTD., Shenzhen (CN)

(72) Inventors: Fuxing Zhang, Shenzhen (CN); Qiao Zou, Shenzhen (CN); Huaibo Yu, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 177 days.

(21) Appl. No.: 14/051,362

(22) Filed: Oct. 10, 2013

(65) Prior Publication Data

US 2014/0039670 A1     Feb. 6, 2014

Related U.S. Application Data

(63) Continuation of application No. PCT/CN2012/073718, filed on Apr. 10, 2012.

(30) Foreign Application Priority Data

Apr. 15, 2011   (CN) .......................... 2011 1 0095496

(51) Int. Cl.
| | | |
|---|---|---|
| *G06F 7/00* | (2006.01) | |
| *G01N 35/02* | (2006.01) | |
| *G01N 35/00* | (2006.01) | |
| *G06F 19/00* | (2011.01) | |

(52) U.S. Cl.
CPC ........ *G01N 35/026* (2013.01); *G01N 35/00613* (2013.01); *G01N 35/00732* (2013.01); *G06F 19/366* (2013.01)

(58) Field of Classification Search
CPC ..................................................... G01N 35/026
USPC ........................................................ 700/228
See application file for complete search history.

(56) References Cited

U.S. PATENT DOCUMENTS

| | | | |
|---|---|---|---|
| 2004/0267562 A1* | 12/2004 | Fuhrer et al. ...................... | 705/2 |
| 2005/0226769 A1 | 10/2005 | Shiga | |
| 2010/0100234 A1* | 4/2010 | Osborne et al. ............... | 700/228 |
| 2011/0022327 A1 | 1/2011 | Busenhart et al. | |

FOREIGN PATENT DOCUMENTS

| | | |
|---|---|---|
| CN | 101276393 A | 10/2008 |
| CN | 201438192 U | 4/2010 |
| WO | WO2006125980 A2 | 11/2006 |

* cited by examiner

*Primary Examiner* — Kyle Logan
(74) *Attorney, Agent, or Firm* — Kory D. Christensen; Stoel Rives LLP

(57) ABSTRACT

A method of processing a sample for an assembly line workstation for a body fluid test includes: receiving application information including a sample number; checking a sample of a sample rack to acquire a sample checking result; matching the sample checking result with the sample number to determine if a match succeeds; and if a match is not successful, pausing dispatch of the sample rack.

17 Claims, 2 Drawing Sheets

SAMPLE PROCESSING METHOD, DEVICE AND SYSTEM FOR AN ASSEMBLY LINE WORKSTATION

TECHNICAL FIELD

This disclosure to a method, device and system for an assembly line workstation for processing body fluid samples.

BACKGROUND

Assembly line workstations for body fluid testing require a high degree of automation, allowing for rapid testing and processing of a large number of test samples. Usually, several doctors use a particular assembly line workstation, making rapid testing a desirable feature.

Three main work models are currently used for an assembly line workstation: (1) a barcode model, which involves matching a sample barcode with patient information; (2) a sample rack model, which relies on a sample position and matching the sample position with patient information; and (3) a sequence model, in which each sample is given a number by the user, after which sample numbers are matched with patient information.

Of the three units mentioned above, the third is most common. Doctors frequently find it to be the most flexible and convenient. However, in current assembly line workstations, this model does not support testing samples in which the sample numbers are not consecutive. For example, the first batch of samples may be given sample numbers 1-100 by the user, while the second batch of samples numbers may be given sample numbers 201-300. If the two batches of samples are placed in an input area, but the user has just applied testing for samples 1-100, the samples numbered 201-300 do not have matched application information. These samples will be pushed to orbit and conveyed to a recovery area. This approach decreases efficiency, since after these samples are conveyed to the recovery area, the user typically needs to take out the samples and retest them.

DETAILED DESCRIPTION

The disclosed sample processing method, device and system for an assembly line workstation increases efficiency and saves time over conventional approaches.

In one embodiment, a sample processing method for an assembly line workstation for body fluid testing includes:

A method of processing a sample for an assembly line workstation for a body fluid test includes: receiving application information including a sample number; checking a sample of a sample rack to acquire a sample checking result; matching the sample checking result with the sample number to determine if a match succeeds; and if a match is not successful, pausing dispatch of the sample rack.

By matching a sample number input by a user with a sample placement situation of the sample rack, when finding a mismatch, the system may pause dispatch of the sample rack, and the user can take an appropriate action to eliminate a mismatch. Compared to conventional approaches, this improves efficiency and saves time.

In one embodiment, a sample processing device for an assembly line workstation for testing body fluid includes an application information receiving unit configured for receiving application information, including a sample number, from a user; a sample rack check unit configured for checking a sample rack and acquiring sample checking result; a match unit, in communication with the information receiving unit and the sample rack check unit, configured for matching the sample checking result with the sample number and determining whether a match succeeds; and a processing unit in communication with a match unit configured to pause the dispatch of the current sample rack when the match is not successful.

In one embodiment, a sample processing system for an assembly line workstation for testing body fluid may include a sample application unit configured for receiving application information from the user, the application input including one or more sample numbers and test items; a testing unit configured for determining application information relating to a sample, matching test items of each samples with sample numbers, determining whether the sample numbers are continuous, and checking whether a sample number matches with a placed sample; and an input unit configured for checking samples in an input area and then dispatching a sample that passed checking from the sample rack input area to a work test area.

Figure 1:
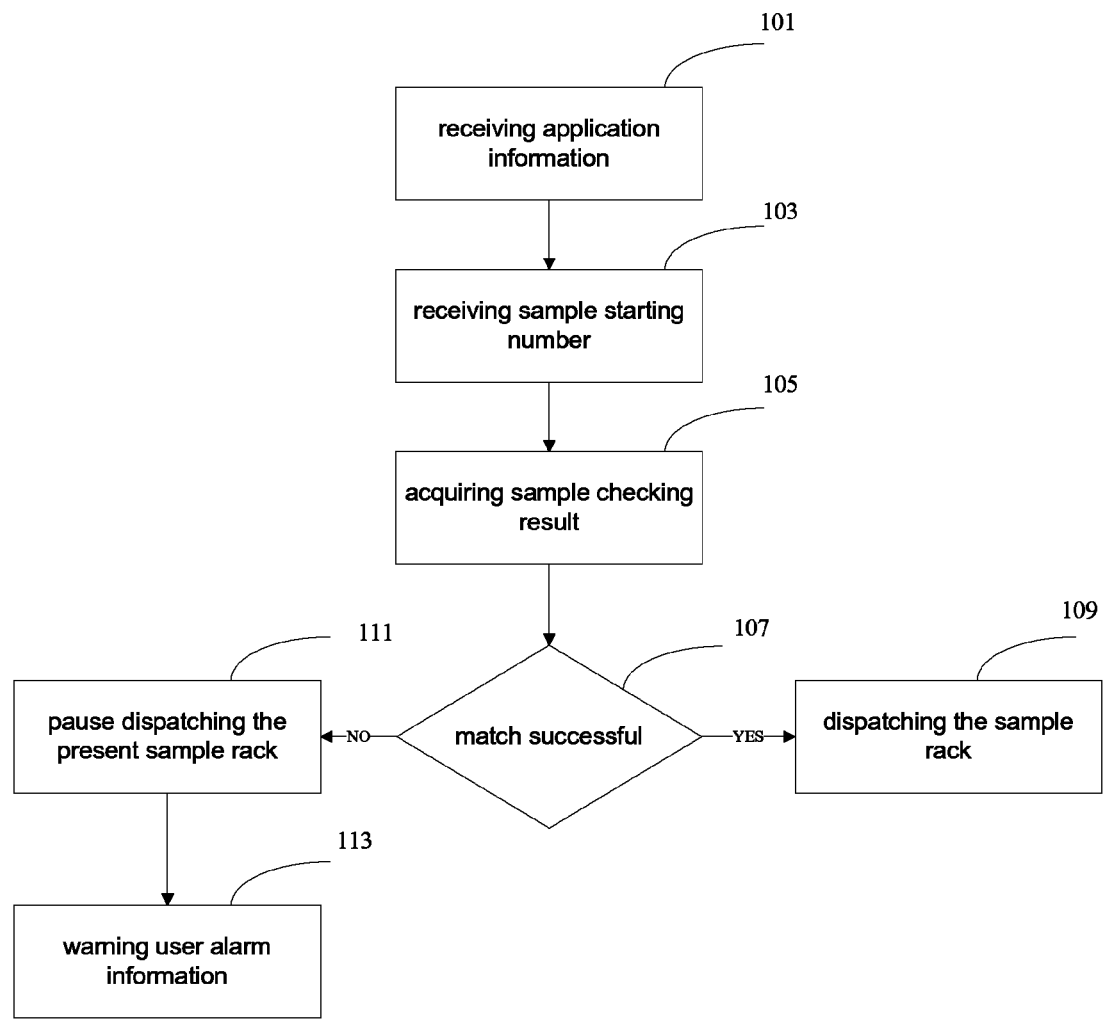
FIG. 1 is a flow chart of an embodiment of a sample processing method for an assembly line workstation.

Referring to FIG. 1, there is shown a flow chart of an embodiment of a sample processing method for an assembly line workstation.

At step 101, application information, usually including one or more sample numbers and selected test items, is received from a user. The selected test items correspond to test information for a sample number, and the sample number matches with the test information in a one-to-one relationship.

At step 103, a sample starting number is received from the user. A user can provide a sample starting number according to the user's needs. For example, the first sample position of #1 sample rack could be #51, actually, based a user's knowledge. In this step, a sample starting number could be set to #51 by the user, so when checking the sample rack, the first sample position of #1 in the sample rack becomes #51. The sample position number of the following sample rack is increased sequentially.

When performing this step, because the user usually sets a number for the first test sample as #1, the sample starting number is usually #1. If the user does not set a starting number, the default sample starting number is #1.

At step 105, the sample loading system checks the sample rack type and the sample rack barcode by scanning the barcode, checks whether there are samples in sample rack using hardware sensors, and acquires a sample rack position number as a sample checking result, e.g., checks whether there is a sample in the first position of the #1 sample rack; if there is, sample position number #1 is communicated to the test unit.

If there is a sample starting number in step 103, then a sequential number is given to the sample position number of the sample rack beginning at the sample starting number. For example, if the sample starting number is #101, then the first sample position number of the first sample rack is #101. If there is a sample in this position, then a sample checking result is acquired as #101, and the following position numbers are increased sequentially. The second position number of the first sample rack is #102, and so on.

If there is no sample starting number in step 103, the sample position number of the sample rack is increased sequentially. If the first sample position of the sample rack is #1, then the second sample position of the sample rack is #2, and so on.

At step 107, the test unit matches the sample checking result with the sample number input by the user, one to one. The matching unit checks whether there is a sample checking result in a sample number input by the user.

Thereafter, it is determined whether the application information input by the user matches with the sample placed by the user. For example, if the sample numbers input by the user are #1-#100, then 100 tests may be applied. After sample loading, the system checks that there are 100 continuous test samples from the starting position. It informs the checking system, after which the checking system will match these 100 samples with 100 tests one to one in order to find a successful match. The match unit when checking the sample rack may have found there is a sample in the sample rack. After acquiring a sample position number of the sample, the match unit will determine whether the sample has the same sample number as in the application information input by the user. If so, the match is successful. If the user applies a test for 100 sample tests of #1-#100 and 10 sample tests of #201-#210, and puts these 110 samples into an input area continuously, the sample loading system checks the previous samples of #1-#100 and will match these 100 samples to test #1-#100. However, if when checking the following 10 samples, the checking unit determines there is no sample application information for sample numbers of #101-#110, this is considered a mismatch.

At step 109, when the matching is successful, the sample loading system dispatches a sample rack from the input area to a test area. There are at least two match methods. According to one method, each sample of each sample rack is matched and dispatched when a match is successful. According to a second method, each sample of all sample racks is matched and dispatched when a match is successful. The illustrated embodiment adopts the first method.

At step 111, when the match is unsuccessful, dispatching the present sample rack is stopped (paused); other sample racks in orbit could continue to be dispatched and are not affected.

In conventional approaches, a mismatched sample rack is conveyed to a test area and, when the sample is not tested, it is conveyed it back to recovery area. By contrast, according to one embodiment, the present sample rack is paused and the mismatch is handled by the user. For example, the user could revise the related information. This significantly saves the user's time and improves efficiency;

As mentioned earlier, the present disclosure dispatches after a match in each sample rack, so when a match is unsuccessful, there is a step of stopping dispatching the sample rack. However, in another match method, that is, dispatching after match each sample of all sample racks, there is no step of stopping dispatching of the present sample rack, because it will not dispatch until matching is successful.

At step 113, when matching is unsuccessful, the user is warned audibly or visually that the present sample does not match the application information. After the user receives the alarm information, the user may proceed correspondingly. For example, if the user confirms that sample is placed by number discontinuously, the sample could be tested after a user process. For instance, in the previous example, when checking that the 101st sample corresponds to the sample position number #101, but the sample number #101 is not applied to test, then after a check by the user, the user may set the sample position #101 as #201 and continue to test.

When a match is unsuccessful, the system may pause the present dispatching sample rack and timely inform the user, allowing the user to process the non-matching sample quickly, improving efficiency and saving time.

Step 105 and step 107 could be exchanged, and the execution sequence could be adjusted.

In the aforementioned embodiment, the sample position number of the sample rack begins from #1 or a sample starting number. Because the sample number may be discontinuous, however, the sample number may be calculated according to a certain method in order to match the sample position number to the corresponding sample number. For example, assume the sample number is 1, 3, 5, 7, 9 . . . , then the method of calculating the sample position number could be set by the user as Y=2*N−1, where Y is the sample position number and N is the sequence number of the sample position. After the user sets the method of calculating the sample position number, then when checking the sample rack, acquiring the sample position number according to this method is the same as the sample checking result. For example, assume the method of calculating the sample position number is Y=2*N−1. If checking the fifth sample position of the first sample rack, the checking result should be Y=2*5−1=9, the sample number is matched, and the application test item that corresponds to sample number 9 is performed. Of course, Y=2*N−1 is merely an example. Different methods for calculating the sample number could be used, e.g., Y=3*N+50, etc.

In some embodiments, receiving the method of calculating the sample position number could be before the sample checking step.

If the sample number is discontinuous, the user may need to input the sample starting number and the method of calculating the sample position number.

Figure 2:
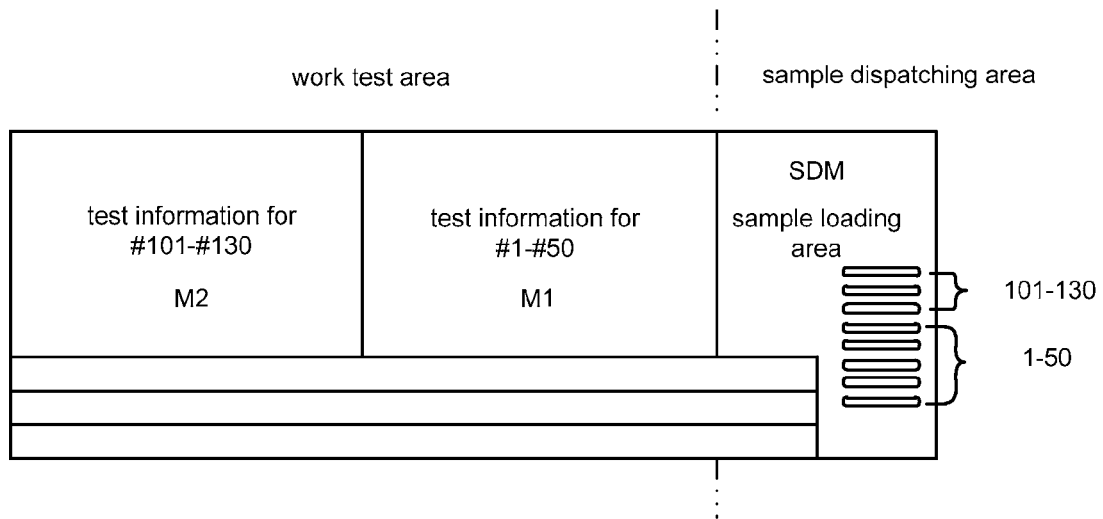
FIG. 2 is a schematic diagram of an embodiment of an assembly line workstation.

FIG. 2 is a schematic diagram of an embodiment of an assembly line workstation. M1 and M2 are units of a body fluid assembly line workstation. SDM is a sample dispatching system. A user may put a sample into the SDM. There may be eight sample racks in the sample input area and there may be 10 samples in each sample rack, so there are 80 samples altogether. The sample numbers are #1-#50 and #101-#130.

A test process according to one embodiment may be as follows.

At step 201, a request is received for applying a sample test by a user. The user may apply test #1-#50 in M1 and apply test #101-#130 in M2.

At step 203, a received sample may be placed in the sample input area by the user. In the current example, 80 samples may be provided. Five sample racks include samples #1-#50, followed by three sample racks including samples #101-#130.

At step 205, when the test begins, after the sample loading unit checks 50 samples, it will match samples #1-#50 with sample test information for #1-#50. After a successful match, the sample rack will be dispatched from the sample dispatching area to M1 for testing.

At step 207, after the previous five sample racks are dispatched, a new sample rack is checked. However, there is no sample application information for #51. As a result, the sample loading unit will pause dispatching of the six sample racks and warn the user about the application information mismatch with the placed sample.

When the user receives the warning information, the user may check the placed sample. If it is found there is a discontinuous test that needs to be tested, then the test may be restarted, and the user may input that the present test begins from sample #101 using a human-computer interaction unit. Thereafter, the checking unit matches samples #101-#130 of the sample rack with the sample test information #101-#130, restarts the dispatching sample rack and tests after a successful match, after which the sample rack is dispatched to a determined analyzer.

Figure 3:
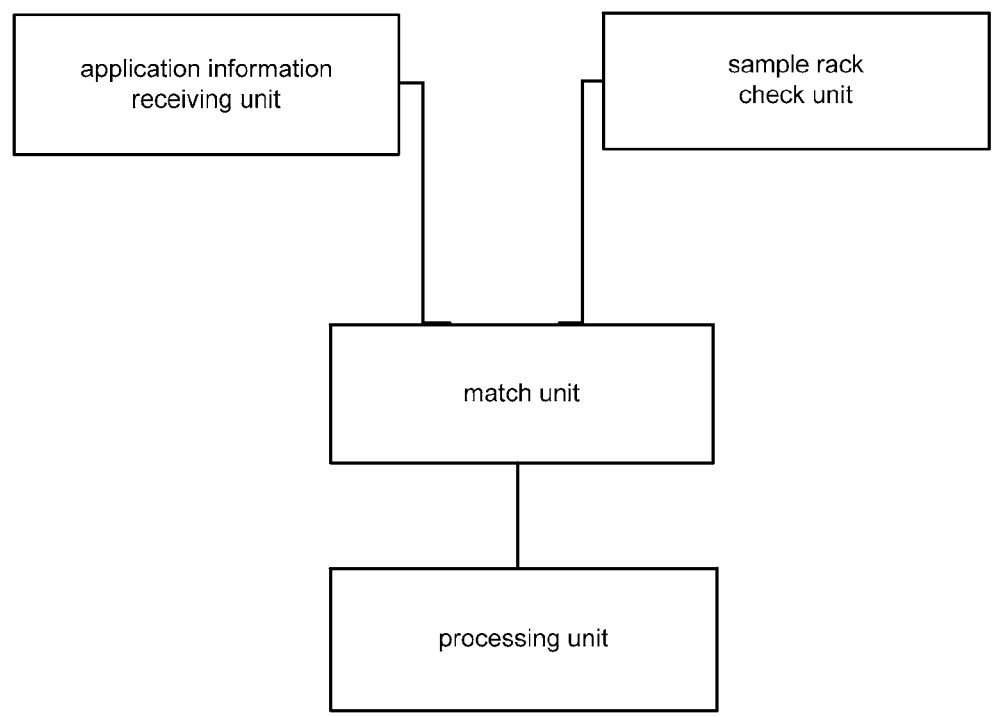
FIG. 3 is schematic diagram of an embodiment of a sample processing device for an assembly line workstation.

FIG. 3 is a schematic diagram of an embodiment of a sample processing device for an assembly line workstation. The device may include: an application information receiving unit 301 configured for receiving application information from a user, the application information including a sample number; a sample rack check unit 303 configured for checking a sample rack and acquiring a sample checking result; a match unit 305 in communication with the information receiving unit 301 and the sample rack check unit 303 configured for matching the sample check result with the sample number and determining whether the match succeeds; and a processing unit 307 in communication with match unit 305 configured to pause the dispatching of the current sample rack when a match is not successful.

In one embodiment, the processing unit 307 is also configured for sending warning information to a user. The warning information may include an image, an audible alert or the like, generated by an interface.

The processing unit may also be configured to start dispatching a sample rack when mismatched. In one embodiment, the match unit 305 is configured for comparing the sample checking result with the sample number In one embodiment, the sample checking unit is configured for checking that there is a sample in the sample rack is configured for acquiring a sample position number of the sample rack as the sample checking result.

The system may also include a sample starting number acquiring unit configured for receiving a sample starting number. The sample rack checking unit may be configured for checking that there is a sample in the sample rack and acquiring a sample position number of the sample rack as the sample checking result.

A method of calculating the sample position number may include: when starting to check the sample of the sample rack, the first position number is the sample starting number; the sample position number of the following sample rack is sequentially numbered to begin from this sample starting number.

In one embodiment, the system also includes a sample number method unit for receiving from the user a method of calculating a sample number. The sample rack checking unit may be configured, for when checking that there is a sample in the sample position, to acquire a sample position number as the sample checking result. The sample position number may be acquired by a method of calculating the sample number input as provided by the user. In one embodiment, the assembly line workstation may operate in a sequential mode.

The present disclosure also provides a sample processing system for an assembly line workstation, including: a sample application unit configured for receiving application information by the user, the application information including a sample number; a testing unit configured for determining application information for the sample, matching test items of each sample with sample numbers, determining whether the sample numbers are continuous, and checking whether a sample number matches with a placed sample; and a sample input unit configured for checking samples in the input area, and then dispatching the sample that passes checking from the sample rack input area to the work test area.

By matching sample number input from the user with sample placement in the sample rack, when a mismatch is found, sample rack dispatching may be paused, allowing the user to perform an appropriate operation to eliminate the mismatch. This improves efficiency and saves time over conventional systems.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternative ways depending upon the particular application or in consideration of any number of cost functions associated with the operation of the system, e.g., one or more of the steps may be deleted, modified or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks and the like), optical storage devices (CD-ROMs, DVDs, Blu-ray discs and the like), flash memory and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage or solution to occur or become more pronounced are not to be construed as a critical, a required or an essential feature or element. As used herein, the terms "comprises," "comprising" and any other variation thereof are intended to cover a non-exclusive inclusion, such that a process, a method, an article or an apparatus that comprises a list of elements does not include only those elements but may include other elements not expressly listed or inherent to such process, method, system, article or apparatus. Also, as used herein, the terms "coupled," "coupling" and any other variation thereof are intended to cover a physical connection, an electrical connection, a magnetic connection, an optical connection, a communicative connection, a functional connection and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. A method of processing a sample for an assembly line workstation for a body fluid test, including: receiving application information including a sample number; checking if there are samples in a sample rack, and, if there are samples in the sample rack, acquiring a sample position number of the sample in the sample rack as a sample checking result; matching the sample checking result with the sample number to determine if a match succeeds; and if a match is not successful, pausing dispatch of the sample rack.

2. The method of claim 1, further comprising: if the match is successful, starting dispatch of the sample rack.

3. The method of claim 1, wherein matching the sample checking result includes: determining whether the sample checking result is the same as the sample number.

4. The method of claim 1, wherein, after the step of receiving application information, the method includes: receiving a sample starting number; and wherein the step of checking the sample of the sample rack includes acquiring the sample position number as a sample checking result; and wherein a first position number of a first sample rack checked is used as the sample starting number, and the sample position number of the following sample rack is sequentially increased in number to begin from the sample starting number.

5. The method of claim 1, wherein, before checking a sample of the sample rack, the step of acquiring the sample checking result includes: receiving user input including a method of calculating the sample number; and wherein the step of checking the sample of the sample rack includes: after checking that there is a sample in the sample rack, acquiring the sample position number as the sample checking result; the sample position number being acquired according to the input method of calculating the sample number.

6. The method of claim 1, wherein the assembly line workstation operates in a sequential mode.

7. The method of claim 1, further comprising: if the match is not successful, outputting warning information to a user.

8. The method of claim 7, wherein warning information includes one or more of a visual warning or an audible warning.

9. A sample processing device for an assembly line workstation for testing body fluids, including: an application information receiving unit configured for receiving application information from a user, the application information including a sample number; a sample rack check unit configured for checking if there are samples in a sample rack, and, if there are samples in the sample rack, acquiring a sample position number of the sample in the sample rack as a sample checking result; a match unit, in communication with the information receiving unit and the sample rack check unit, configured for matching the sample check result with the sample number and determining whether the match is successful; and a processing unit, in communication with the match unit, configured for pausing dispatch of the sample rack when match is not successful.

10. The device of claim 9, wherein the processing unit is also configured to start dispatch of the sample rack when the match is successful.

11. The device of claim 9, wherein the match unit is configured for determining whether the sample checking result matches the sample number.

12. The device of claim 9, further including: a sample starting number acquiring unit configured for receiving a sample starting number from a user; wherein the sample checking unit is configured, when checking whether there is a sample in the sample rack, to acquire the sample position number as the sample checking result; and wherein a method of calculating the sample position number is: the first position number of the first sample rack checked is set as the sample starting number, and the sample position number of the following sample rack is sequentially increased in number beginning from the sample starting number.

13. The device of claim 9, further including: A sample number method unit configured for receiving from a user a method of calculating the sample number; and wherein the sample checking unit is configured, when checking whether there is a sample in the sample rack, to acquire the sample position number as the sample checking result; and wherein the sample position number is acquired according to the method of calculating the sample number provided by the user.

14. The device of claim 9, wherein the assembly line workstation operates in a sequential mode.

15. A system for processing samples in an assembly line workstation for testing body fluids, including: a sample application unit configured for receiving application information from a user, the application information including a sample number; a testing unit configured for determining application information of a sample, matching test items of each sample with sample numbers, determining whether the sample numbers are continuous, and checking whether a sample number matches with the placed sample; and a sample input unit configured for checking samples in an input area, then dispatching the samples that passed checking from the sample rack input area to the work test area.

16. The system of claim 9, wherein the processing unit is further configured for outputting warning information to the user when the match is unsuccessful.

17. The device of claim 16, wherein the warning information includes one or more of an image or a sound.

* * * * *